(12) United States Patent
Mosa et al.

(10) Patent No.: US 11,220,666 B2
(45) Date of Patent: Jan. 11, 2022

(54) BACTERIAL STRAIN CLOSTRIDIUM HISTOLYTICUM AND METHODS OF USE THEREOF

(71) Applicant: MB Pharma s.r.o., Prague (CZ)

(72) Inventors: Marek Mosa, Meceriz (CZ); Martin Benesik, Strani (CZ)

(73) Assignee: MB Pharma s.r.o., Prague (CZ)

( * ) Notice: Subject to any disclaimer, the term of this patent is extended or adjusted under 35 U.S.C. 154(b) by 0 days.

(21) Appl. No.: 16/646,874

(22) PCT Filed: Sep. 11, 2018

(86) PCT No.: PCT/CZ2018/000044
§ 371 (c)(1),
(2) Date: Mar. 12, 2020

(87) PCT Pub. No.: WO2019/052586
PCT Pub. Date: Mar. 21, 2019

(65) Prior Publication Data
US 2020/0339941 A1  Oct. 29, 2020

(30) Foreign Application Priority Data
Sep. 13, 2017 (CZ) .............................. PV 2017-537

(51) Int. Cl.
*C12N 1/20* (2006.01)
*C12N 5/071* (2010.01)
*C12N 9/64* (2006.01)

(52) U.S. Cl.
CPC ............. *C12N 1/20* (2013.01); *C12N 5/0676* (2013.01); *C12N 9/6448* (2013.01); *C12N 9/6472* (2013.01); *C12N 9/6491* (2013.01); *C12Y 304/22008* (2013.01); *C12Y 304/24007* (2013.01)

(58) Field of Classification Search
None
See application file for complete search history.

(56) References Cited

U.S. PATENT DOCUMENTS

2011/0294192 A1* 12/2011 Fukushima ............ C07K 14/78
435/220

FOREIGN PATENT DOCUMENTS

| EP | 0468411 A2 | 1/1992 | |
|---|---|---|---|
| EP | 2363461 A1 | 9/2011 | |
| WO | WO-2010058707 A1 * | 5/2010 | ............... C12N 9/52 |
| WO | WO 2013/106510 | 7/2013 | |
| WO | WO 2019/052586 | 3/2019 | |

OTHER PUBLICATIONS

Uniprot, Accession No. Q46085, 2017, www.uniprot.org. (Year: 2017).*
Uniprot, Accession No. Q9X721, 2017, www.uniprot.org. (Year: 2017).*
Dargatz et al., The heterodimeric protease clostripain from Clostridium histolyticum in encoded by a single gene, Mol. Gen. Genet. 240, 1993, 140-45. (Year: 1993).*
Berkova, Z., et al., "Testing of a New Collagenase Blend for Pancreatic Islet Produced by Clostridium Hystolyticum," Advances in Biosciences and Biotechnology, 9.11 (2018): 26-35.
Berkova, Z., et al., "The Impact of Islet Labeling with Superparamagnetic Nanoparticles for Magnetic Resonance Imaging on Islet Vitality," 10th World Congress of IPITA, Geneva, Switzerland, May 4-7, 2005.
Berman S., Lewenthal J.P., Webster M. E., Altieri P.L. and Gochenour R.B., "Factors Affecting the Elaboration by Clostridium Histolyticum of Proteinases Capable of Debriding Third Degree Burn Eschars on Guinea Pigs," Journal of Bacteriology 82.4 (1961): 582-88.
Bond, M. D. and H. E. Van Wart, "Characterization of the Individual Collagenases from Clostridium Histolyticum," Biochemistry 19 (1984): 3085-91.
Dendo, M., Maeda, H., Yamagata, Y., Murayama, K., Watanabe, K., Imura, T., Inagaki, A., Igarashi, Y., Katoh, Y., Ebina, M., Fujimori, K., Igarashi, K., Ohuchi, N., Satomi, S., Goto, M., "Synergistic Effect of Neutral Protease and Clostripain on Rat Pancreatic Islet Isolation," Transplantation 99(7) (2015): 1349-55.
De Vos, P., Smink, AM., Paredes, G., et al., "Enzymes for Pancreatic Islet Isolation Impact Chemokine-Production and Polarization of Insulin-Producing β-Cells with Reduced Functional Survival of Immunoisolated Rat Islet-Allografts as a Consequence," Blondeau B, ed. PLoS One 11(1) (2016): 1-18.
Dragosits, M., Mattanovich, D., "Adaptive Laboratory Evolution—Principles and Applications for Biotechnology," Microbial Cell Factories (2013): 12:64.
Indra, D., K. Ramalingam, and M. Babu, "Isolation, Purification and Characterization of Collagenase from Hepatopancreas of the Land Snail Achatina Fulica," Comparative Biochemistry and Physiology Part B: Biochemistry and Molecular Biology 142.1 (2005): 1-7.
International Preliminary Report on Patentability for PCT App. No. PCT/CZ2018/000044 dated Nov. 12, 2019.
Kin, Tatsuya, Johnson, P., Shapiro, A.M., Lakey, J., "Factors Influencing the Collagenase Digestion Phase of Human Islet Isolation," Transplantation, 83(1) (2007): 7-12.

(Continued)

*Primary Examiner* — Robert B Mondesi
*Assistant Examiner* — Todd M Epstein
(74) *Attorney, Agent, or Firm* — Mark S. Cohen; Pearl Cohen Zedek Latzer Baratz LLP (57) ABSTRACT

Bacterial strain *Clostridium histolyticum* was deposited in CCM (Czech Collection of Microorganisms at Masaryk University, Faculty of Science) under No. CCM 8656. This strain produces proteolytic enzymes including collagenase, elastinase, neutral proteases and clostripain under anaerobic conditions at a temperature from 25° C. to 45° C. The strain is used for the production of a mixture of two collagenases, col 1 and col 2, with molecular weight 116 kDa and 126 kDa, and possibly clostripain. The mixture of the above-mentioned collagenases and possibly clostripain obtained from the above-mentioned strain is used for the isolation of Langerhans islets.

5 Claims, 2 Drawing Sheets
Specification includes a Sequence Listing.

(56) References Cited

OTHER PUBLICATIONS

Klimova, O.A., S.I. Borukhov, N.I. Solovyeva, T.O. Balaevskaya and A.Y. Strongin, "The Isolation and Properties of Collagenolytic Proteases from Crab Hepatopancreas," Biochem. Biophys. Res. Commun. 166 (1990): 1411-20.

Maclennan, John D., I. Mandl, and E. L. Howes, "Bacterial Digestion of Collagen," The Journal of Clinical Investigation 32.12 (1953): 1317-22.

Matsushita, O., Jung, C-M., Katayama, S., Minami, J., Takahashi, Y., Okabe, A., "Gene Duplication and Multiplicity of Collagenases in Clostridium Histolyticum," Journal of Bacteriology 181.3 (1999): 923-33.

Matsushita, O., K. Yoshihara, S.I. Katayama, J. Minami and A. Okabe, "Purification and Characterization of a Clostridium Perfringens 120-Kilodalton Collagenase and Nucleotide Sequence of the Corresponding Gene," J. Bacteriol. 176 (1994): 149-56.

Mookhtair, K.A. and Van Wart, H.E., "Clostridium Histolyticum Collagenases: A New Look at Some Old Enzymes," Matrix 1 (1992) 116-26.

Sakamoto, S., P. Goldhaber and M.J. Glimcher, "The Further Purification and Characterization of Mouse Bone Collagenase," Calcified Tissue Res. 10 (1972): 142-51.

Search Report and Written Opinion for PCT App. No. PCT/CZ2018/000044 dated Mar. 21, 2019.

Takahashi, S. and Seifter, S., "New Culture Conditions for Clostridium histolyticum leading to Production of Collagenase of High Specific Activity," J. Appl. Bact. 35 (1972): 647-57.

Yoshida, E. and H. Noda, "Isolation and Characterization of Collagenase I and II from Clostridium Histolyticum," Biochem. Biophys. Acta (BBA)-Enzymology and Biological Oxidation, 105.3 (1965): 562-74.

Yoshihara, K., Matsushita, O., Minami, J., Okabe, A., "Cloning and Nucleotide Sequence Analysis of the colH Gene from Clostridium Histolyticum Encoding a Collagenase and a Gelatinase," Journal of Bacteriology 176.21 (1994): 6489-96.

\* cited by examiner

SEQUENCE LISTING

```
<160> NUMBER OF SEQ ID NOS: 2

<210> SEQ ID NO 1
<211> LENGTH: 1021
<212> TYPE: PRT
<213> ORGANISM: Clostridium histolyticum

<400> SEQUENCE: 1

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
            20                  25                  30

Asp Lys Asn Asn Ala Thr Ala Ala Val Gln Asn Glu Ser Lys Arg Tyr
        35                  40                  45

Thr Val Ser Tyr Leu Lys Thr Leu Asn Tyr Tyr Asp Leu Val Asp Leu
    50                  55                  60

Leu Val Lys Thr Glu Ile Glu Asn Leu Pro Asp Leu Phe Gln Tyr Ser
65                  70                  75                  80

Ser Asp Ala Lys Glu Phe Tyr Gly Asn Lys Thr Arg Met Ser Phe Ile
                85                  90                  95

Met Asp Glu Ile Gly Arg Arg Ala Pro Gln Tyr Thr Glu Ile Asp His
            100                 105                 110

Lys Gly Ile Pro Thr Leu Val Glu Val Val Arg Ala Gly Phe Tyr Leu
        115                 120                 125

Gly Phe His Asn Lys Glu Leu Asn Glu Ile Asn Lys Arg Ser Phe Lys
    130                 135                 140

Glu Arg Val Ile Pro Ser Ile Leu Ala Ile Gln Lys Asn Pro Asn Phe
145                 150                 155                 160

Lys Leu Gly Thr Glu Val Gln Asp Lys Ile Val Ser Ala Thr Gly Leu
                165                 170                 175

Leu Ala Gly Asn Glu Thr Ala Pro Pro Glu Val Val Asn Asn Phe Thr
            180                 185                 190

Pro Ile Leu Gln Asp Cys Ile Lys Asn Ile Asp Arg Tyr Ala Leu Asp
        195                 200                 205

Asp Leu Lys Ser Lys Ala Leu Phe Asn Val Leu Ala Ala Pro Thr Tyr
    210                 215                 220

Asp Ile Thr Glu Tyr Leu Arg Ala Thr Lys Glu Lys Pro Glu Asn Thr
225                 230                 235                 240

Pro Trp Tyr Gly Lys Ile Asp Gly Phe Ile Asn Glu Leu Lys Lys Leu
                245                 250                 255

Ala Leu Tyr Gly Lys Ile Asn Asp Asn Asn Ser Trp Ile Ile Asp Asn
            260                 265                 270
```

-continued

```
Gly Ile Tyr His Ile Ala Pro Leu Gly Lys Leu His Ser Asn Asn Lys
            275                 280                 285

Ile Gly Ile Glu Thr Leu Thr Glu Val Met Lys Val Tyr Pro Tyr Leu
    290                 295                 300

Ser Met Gln His Leu Gln Ser Ala Asp Gln Ile Lys Arg His Tyr Asp
305                 310                 315                 320

Ser Lys Asp Ala Glu Gly Asn Lys Ile Pro Leu Asp Lys Phe Lys Lys
                325                 330                 335

Glu Gly Lys Glu Lys Tyr Cys Pro Lys Thr Tyr Thr Phe Asp Asp Gly
            340                 345                 350

Lys Val Ile Ile Lys Ala Gly Ala Arg Val Glu Glu Lys Val Lys
            355                 360                 365

Arg Leu Tyr Trp Ala Ser Lys Glu Val Asn Ser Gln Phe Phe Arg Val
    370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Glu
            420                 425                 430

Gly Thr Phe Phe Thr Tyr Glu Arg Glu Ala Gln Glu Ser Thr Tyr Thr
    435                 440                 445

Leu Glu Glu Leu Phe Arg His Glu Tyr Thr His Tyr Leu Gln Gly Arg
    450                 455                 460

Tyr Ala Val Pro Gly Gln Trp Gly Arg Thr Lys Leu Tyr Asp Asn Asp
465                 470                 475                 480

Arg Leu Thr Trp Tyr Glu Glu Gly Gly Ala Glu Leu Phe Ala Gly Ser
                485                 490                 495

Thr Arg Thr Ser Gly Ile Leu Pro Arg Lys Ser Ile Val Ser Asn Ile
            500                 505                 510

His Asn Thr Thr Arg Asn Asn Arg Tyr Lys Leu Ser Asp Thr Val His
    515                 520                 525

Ser Lys Tyr Gly Ala Ser Phe Glu Phe Tyr Asn Tyr Ala Cys Met Phe
530                 535                 540

Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
                565                 570                 575

Asp Leu Ser Ser Asn Tyr Ala Leu Asn Asp Lys Tyr Gln Asp His Met
            580                 585                 590

Gln Glu Arg Ile Asp Asn Tyr Glu Asn Leu Thr Val Pro Phe Val Ala
    595                 600                 605

Asp Asp Tyr Leu Val Arg His Ala Tyr Lys Asn Pro Asn Glu Ile Tyr
    610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670

Phe Ile Asp Asp Ser Leu Lys Lys Leu Asp Thr Tyr Ser Trp Ser Gly
    675                 680                 685

Tyr Lys Thr Leu Thr Ala Tyr Phe Thr Asn Tyr Lys Val Asp Ser Ser
```

```
            690                 695                 700
Asn Arg Val Thr Tyr Asp Val Phe His Gly Tyr Leu Pro Asn Glu
705                 710                 715                 720

Gly Asp Ser Lys Asn Ser Leu Pro Tyr Gly Lys Ile Asn Gly Thr Tyr
                725                 730                 735

Lys Gly Thr Glu Lys Glu Lys Ile Lys Phe Ser Ser Glu Gly Ser Phe
                740                 745                 750

Asp Pro Asp Gly Lys Ile Val Ser Tyr Glu Trp Asp Phe Gly Asp Gly
                755                 760                 765

Asn Lys Ser Asn Glu Glu Asn Pro Glu His Ser Tyr Asp Lys Val Gly
770                 775                 780

Thr Tyr Thr Val Lys Leu Lys Val Thr Asp Asp Lys Gly Glu Ser Ser
785                 790                 795                 800

Val Ser Thr Thr Thr Ala Glu Ile Lys Asp Leu Ser Glu Asn Lys Leu
                805                 810                 815

Pro Val Ile Tyr Met His Val Pro Lys Ser Gly Ala Leu Asn Gln Lys
                820                 825                 830

Val Val Phe Tyr Gly Lys Gly Thr Tyr Asp Pro Asp Gly Ser Ile Ala
                835                 840                 845

Gly Tyr Gln Trp Asp Phe Gly Asp Gly Ser Asp Phe Ser Ser Glu Gln
                850                 855                 860

Asn Pro Ser His Val Tyr Thr Lys Lys Gly Glu Tyr Thr Val Thr Leu
865                 870                 875                 880

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
                900                 905                 910

Asn Ser Lys Glu Thr Ala Ser Gly Pro Ile Val Pro Gly Ile Pro Val
                915                 920                 925

Ser Gly Thr Ile Glu Asn Thr Ser Asp Gln Asp Tyr Phe Tyr Phe Asp
                930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
                980                 985                 990

Lys Pro Gly Arg Tyr Tyr Ile His Leu Tyr Met Phe Asn Gly Ser Tyr
                995                 1000                1005

Met Pro Tyr Arg Ile Asn Ile Glu Gly Ser Val Gly Arg
   1010                1015                1020

<210> SEQ ID NO 2
<211> LENGTH: 1118
<212> TYPE: PRT
<213> ORGANISM: Clostridium histolyticum

<400> SEQUENCE: 2

Met Lys Lys Asn Ile Leu Lys Ile Leu Met Asp Ser Tyr Ser Lys Glu
1               5                   10                  15

Ser Lys Ile Gln Thr Val Arg Arg Val Thr Ser Val Ser Leu Leu Ala
                20                  25                  30

Val Tyr Leu Thr Met Asn Thr Ser Ser Leu Val Leu Ala Lys Pro Ile
            35                  40                  45
```

-continued

```
Glu Asn Thr Asn Asp Thr Ser Ile Lys Asn Val Glu Lys Leu Arg Asn
 50                  55                  60

Ala Pro Asn Glu Glu Asn Ser Lys Lys Val Glu Asp Ser Lys Asn Asp
 65                  70                  75                  80

Lys Val Glu His Val Lys Asn Ile Glu Glu Ala Lys Val Glu Gln Val
                 85                  90                  95

Ala Pro Glu Val Lys Ser Lys Ser Thr Leu Arg Ser Ala Ser Ile Ala
                100                 105                 110

Asn Thr Asn Ser Glu Lys Tyr Asp Phe Glu Tyr Leu Asn Gly Leu Ser
                115                 120                 125

Tyr Thr Glu Leu Thr Asn Leu Ile Lys Asn Ile Lys Trp Asn Gln Ile
    130                 135                 140

Asn Gly Leu Phe Asn Tyr Ser Thr Gly Ser Gln Lys Phe Phe Gly Asp
145                 150                 155                 160

Lys Asn Arg Val Gln Ala Ile Ile Asn Ala Leu Gln Glu Ser Gly Arg
                165                 170                 175

Thr Tyr Thr Ala Asn Asp Met Lys Gly Ile Glu Thr Phe Thr Glu Val
                180                 185                 190

Leu Arg Ala Gly Phe Tyr Leu Gly Tyr Tyr Asn Asp Gly Leu Ser Tyr
    195                 200                 205

Leu Asn Asp Arg Asn Phe Gln Asp Lys Cys Ile Pro Ala Met Ile Ala
210                 215                 220

Ile Gln Lys Asn Pro Asn Phe Lys Leu Gly Thr Ala Val Gln Asp Glu
225                 230                 235                 240

Val Ile Thr Ser Leu Gly Lys Leu Ile Gly Asn Ala Ser Ala Asn Ala
                245                 250                 255

Glu Val Val Asn Asn Cys Val Pro Val Leu Lys Gln Phe Arg Glu Asn
                260                 265                 270

Leu Asn Gln Tyr Ala Pro Asp Tyr Val Lys Gly Thr Ala Val Asn Glu
    275                 280                 285

Leu Ile Lys Gly Ile Glu Phe Asp Phe Ser Gly Ala Ala Tyr Glu Lys
290                 295                 300

Asp Val Lys Thr Met Pro Trp Tyr Gly Lys Ile Asp Pro Phe Ile Asn
305                 310                 315                 320

Glu Leu Lys Ala Leu Gly Leu Tyr Gly Asn Ile Thr Ser Ala Thr Glu
                325                 330                 335

Trp Ala Ser Asp Val Gly Ile Tyr Tyr Leu Ser Lys Phe Gly Leu Tyr
                340                 345                 350

Ser Thr Asn Arg Asn Asp Ile Val Gln Ser Leu Glu Lys Ala Val Asp
    355                 360                 365

Met Tyr Lys Tyr Gly Lys Ile Ala Phe Val Ala Met Glu Arg Ile Thr
370                 375                 380

Trp Asp Tyr Asp Gly Ile Gly Ser Asn Gly Lys Lys Val Asp His Asp
385                 390                 395                 400

Lys Phe Leu Asp Asp Ala Glu Lys His Tyr Leu Pro Lys Thr Tyr Thr
                405                 410                 415

Phe Asp Asn Gly Thr Phe Ile Ile Arg Ala Gly Asp Lys Val Ser Glu
                420                 425                 430

Glu Lys Ile Lys Arg Leu Tyr Trp Ala Ser Arg Glu Val Lys Ser Gln
    435                 440                 445

Phe His Arg Val Val Gly Asn Asp Lys Ala Leu Glu Val Gly Asn Ala
450                 455                 460

Asp Asp Val Leu Thr Met Lys Ile Phe Asn Ser Pro Glu Glu Tyr Lys
```

-continued

```
            465                 470                 475                 480
        Phe Asn Thr Asn Ile Asn Gly Val Ser Thr Asp Asn Gly Gly Leu Tyr
                        485                 490                 495

Ile Glu Pro Arg Gly Thr Phe Tyr Thr Tyr Glu Arg Thr Pro Gln Gln
                        500                 505                 510

Ser Ile Phe Ser Leu Glu Glu Leu Phe Arg His Glu Tyr Thr His Tyr
                        515                 520                 525

Leu Gln Ala Arg Tyr Leu Val Asp Gly Leu Trp Gly Gln Gly Pro Phe
                    530                 535                 540

Tyr Glu Lys Asn Arg Leu Thr Trp Phe Asp Glu Gly Thr Ala Glu Phe
        545                 550                 555                 560

Phe Ala Gly Ser Thr Arg Thr Ser Gly Val Leu Pro Arg Lys Ser Ile
                        565                 570                 575

Leu Gly Tyr Leu Ala Lys Asp Lys Val Asp His Arg Tyr Ser Leu Lys
                        580                 585                 590

Lys Thr Leu Asn Ser Gly Tyr Asp Asp Ser Asp Trp Met Phe Tyr Asn
                        595                 600                 605

Tyr Gly Phe Ala Val Ala His Tyr Leu Tyr Glu Lys Asp Met Pro Thr
                    610                 615                 620

Phe Ile Lys Met Asn Lys Ala Ile Leu Asn Thr Asp Val Lys Ser Tyr
        625                 630                 635                 640

Asp Glu Ile Ile Lys Lys Leu Ser Asp Asp Ala Asn Lys Asn Thr Glu
                        645                 650                 655

Tyr Gln Asn His Ile Gln Glu Leu Ala Asp Lys Tyr Gln Gly Ala Gly
                        660                 665                 670

Ile Pro Leu Val Ser Asp Asp Tyr Leu Lys Asp His Gly Tyr Lys Lys
                        675                 680                 685

Ala Ser Glu Val Tyr Ser Glu Ile Ser Lys Ala Ala Ser Leu Thr Asn
                    690                 695                 700

Thr Ser Val Thr Ala Glu Lys Ser Gln Tyr Phe Asn Thr Phe Thr Leu
        705                 710                 715                 720

Arg Gly Thr Tyr Thr Gly Glu Thr Ser Lys Gly Glu Phe Lys Asp Trp
                        725                 730                 735

Asp Glu Met Ser Lys Lys Leu Asp Gly Thr Leu Glu Ser Leu Ala Lys
                        740                 745                 750

Asn Ser Trp Ser Gly Tyr Lys Thr Leu Thr Ala Tyr Phe Thr Asn Tyr
                    755                 760                 765

Arg Val Thr Ser Asp Asn Lys Val Gln Tyr Asp Val Val Phe His Gly
                    770                 775                 780

Val Leu Thr Asp Asn Ala Asp Ile Ser Asn Asn Lys Ala Pro Ile Ala
        785                 790                 795                 800

Lys Val Thr Gly Pro Ser Thr Gly Ala Val Gly Arg Asn Ile Glu Phe
                        805                 810                 815

Ser Gly Lys Asp Ser Lys Asp Glu Asp Gly Lys Ile Val Ser Tyr Asp
                        820                 825                 830

Trp Asp Phe Gly Asp Gly Ala Thr Ser Arg Gly Lys Asn Ser Val His
                    835                 840                 845

Ala Tyr Lys Lys Ala Gly Thr Tyr Asn Val Thr Leu Lys Val Thr Asp
                    850                 855                 860

Asp Lys Gly Ala Thr Ala Thr Glu Ser Phe Thr Ile Glu Ile Lys Asn
        865                 870                 875                 880

Glu Asp Thr Thr Thr Pro Ile Thr Lys Glu Met Glu Pro Asn Asp Asp
                        885                 890                 895
```

```
Ile Lys Glu Ala Asn Gly Pro Ile Val Glu Gly Val Thr Val Lys Gly
            900                 905                 910

Asp Leu Asn Gly Ser Asp Asp Ala Asp Thr Phe Tyr Phe Asp Val Lys
            915                 920                 925

Glu Asp Gly Asp Val Thr Ile Glu Leu Pro Tyr Ser Gly Ser Ser Asn
    930                 935                 940

Phe Thr Trp Leu Val Tyr Lys Glu Gly Asp Asp Gln Asn His Ile Ala
945                 950                 955                 960

Ser Gly Ile Asp Lys Asn Asn Ser Lys Val Gly Thr Phe Lys Ser Thr
                965                 970                 975

Lys Gly Arg His Tyr Val Phe Ile Tyr Lys His Asp Ser Ala Ser Asn
            980                 985                 990

Ile Ser Tyr Ser Leu Asn Ile Lys  Gly Leu Gly Asn Glu  Lys Leu Lys
            995                 1000                 1005

Glu Lys  Glu Asn Asn Asp Ser  Ser Asp Lys Ala Thr  Val Ile Pro
    1010                 1015                 1020

Asn Phe  Asn Thr Thr Met Gln  Gly Ser Leu Leu Gly  Asp Asp Ser
    1025                 1030                 1035

Arg Asp  Tyr Tyr Ser Phe Glu  Val Lys Glu Glu Gly  Glu Val Asn
    1040                 1045                 1050

Ile Glu  Leu Asp Lys Lys Asp  Glu Phe Gly Val Thr  Trp Thr Leu
    1055                 1060                 1065

His Pro  Glu Ser Asn Ile Asn  Asp Arg Ile Thr Tyr  Gly Gln Val
    1070                 1075                 1080

Asp Gly  Asn Lys Val Ser Asn  Lys Val Lys Leu Arg  Pro Gly Lys
    1085                 1090                 1095

Tyr Tyr  Leu Leu Val Tyr Lys  Tyr Ser Gly Ser Gly  Asn Tyr Glu
    1100                 1105                 1110

Leu Arg  Val Asn Lys
    1115
```

BACTERIAL STRAIN CLOSTRIDIUM HISTOLYTICUM AND METHODS OF USE THEREOF

CROSS-REFERENCE TO RELATED APPLICATIONS

This application is a National Phase Application of PCT International Application No. PCT/CZ2018/000044, International Filing Date Sep. 11, 2018, claiming priority to CZ Patent Application No. PV 2017-537, filed on Sep. 13, 2017, which are hereby incorporated by reference.

SEQUENCE LISTING

The instant application contains a Sequence Listing which has been submitted electronically in ASCII format and is hereby incorporated by reference in its entirety. Said ASCII copy, created on Mar. 9, 2020, is named P-593693-US_ST25-12MAR20.txt and is 18,753 bytes in size.

FIELD OF THE INVENTION

The invention is based on the new strain of bacterium *Clostridium histolyticum*, methods of using it for the production of crude collagenase with a high yield, methods of preparing collagenase using this strain and the application of the collagenase for the isolation of Langerhans islets.

BACKGROUND OF THE INVENTION

Collagenase is a protease which is able to degrade the collagen protein (the basic component of intercellular mass, e.g., in connective tissue). Collagenases are commonly used in research, particularly for the disintegration of intercellular mass to release cells. In this respect, clostridiopeptidase A isolated from *Clostridium histolyticum* proved to be useful (the name of the bacterium, i.e., histolyticum, reflects its ability to degrade tissues). Enzyme collagenase is not only used for research purposes; it has also found its place in human and veterinary medicine, especially for the treatment of skin diseases. In connection with certain non-specific proteases, the collagenase removes necrotic tissue from wounds and thus accelerates healing and improves epithelialization. Collagenase is used in tissue transplantation and for tissue disintegration. It is also applied for the treatment of (acid) burns of various degrees, decubiti, skin ulcers, scabs, etc. Not only is the epithelialization of skin fast and effective after treatment with collagenase, but also the collagenase treatment prevents formation of keloids (enlarged scars of tumour-like appearance) and hypertrophic growth as a result of the formation of decomposed collagen.

Various strains of microorganisms, cultured under defined conditions, are known to synthesize collagenase. It was found that among all organisms that are able to synthesize collagenase, *Clostridium histolyticum* is the best producer. MacLennan J. D., Mandl I. and Howes E. I.: Bacterial digestion of collagen. J. Clin. Inv. 32: 1317-1322 (1953) described conditions needed for growth of *Clostridium histolyticum*. They examined the composition of the liquid environment which mainly consists of proteose peptone, inorganic salts and a vitamin solution. Bacteria are cultured at 37° C. and pH 7.2. Berman S., Lewenthal J. P., Webster M. E., Altieri P. L. and Gochenour R. B.: Factors affecting the elaboration by *Clostridium histolyticum* of proteinases capable of debriding third degree burn eschars on guinea pigs. J. Bacteriol. 82: 582-588 (1961) also examined growth conditions of *Clostridium histolyticum* with the aim to produce collagenase. They were successful in culturing of *Clostridium histolyticum* in medium which did not contain any inorganic salts; it only contained proteose peptone, enzymatically hydrolysed proteins of casein and soya (soya culture medium) and a vitamin solution. Such a composition of culture medium also determined other parameters of conditions required for satisfactory growth and biosynthesis of collagenase, such as the value of pH 8.5 and a temperature 30° C. and higher.

*Clostridium histolyticum* is an anaerobic bacterium and anaerobic conditions must be ensured for culturing of this bacterium in a liquid environment. Takahashi S. and Seifert S.: J. Appl. Bact. 35, 47 (1972) used the reducing agents sodium thioglycolate and sodium bisulfite in order to achieve the anaerobic conditions necessary for bacterial growth. The optimum results, i.e., the highest yield of collagenase, was achieved when the above-mentioned reducing agents were used in the ratio of 1:1.

Up to the present, a considerable number of procedures using various buffering systems (and mostly including precipitation for the isolation of a functional protein) have been applied for collagenase extraction from different sources (both bacterial and other). However, these procedures are performed at physiological pH 7.4-7.6, which is not optimal for the production of bacterial collagenase and at a low temperature which prevents degradation of the enzyme. The essence is that commonly used physiological pH is not the most suitable for *Clostridium*. E.g., Yoshida, E. and H. Noda, 1965. Isolation and characterization of collagenase I and II from *Clostridium histolyticum*. Biochim Biophys. Acta, 10593: 562-574. DOI: 10.1016/S0926-6593(65) 80239-9; or Sakamoto, S., P. Goldhaber and M. J. Glimcher, 1972. The further purification and characterization of mouse bone collagenase. Calc. Tis. Res., 10: 142-151. DOI: 10.1007/BF02012544; or Bond, M. D. and H. E. Van Wart, 1984. Characterization of the individual collagenases from *Clostridium histolyticum*. Biochemistry, 19: 3085-3091. DOI: 10.1021/bi00308 a036; or Matsushita, O., K. Yoshihara, S. I. Katayama, J. Minami and A. Okabe, 1994. Purification and characterization of a *Clostridium perfringens* 120-Kilodalton collagenase and nucleotide sequence of the corresponding gene. J. Bacteriol., 176: 149-156. PMCID: PMC205026.

Buffers other than Tris-HCl are also used for the purification of collagenase, e.g., sodium bicarbonate, which also should maintain the stability of collagenase. In bicarbonate buffers, a higher pH is used, which is in our case suitable for collagenase from *Clostridium histolyticum*; however, in such purification protocols, the collagenase is isolated from snails. Indra, D., K. Ramalingam and M. Babu, 2005. Isolation, purification and characterization of collagenase from hepatopancreas of the land snail Achatina fulica. Comparative Biochem. Phys., 142: 1-7. DOI: 10.1016/J.CBPC.2005.02.004.

The amounts of used ions appropriate for stability and effective action of enzymes degrading extracellular components are different in the particular approaches. Klimova, O. A., S. I. Borukhov, N. I. Solovyeva, T. O. Balaevskaya and A. Y. Strongin, 1990. The isolation and properties of collagenolytic proteases from crab hepatopancreas. Biochem. Biophys. Res. Commun., 166: 1411-1420. DOI: 10.1016/0006-291x(90)91024-M.

By combining the use of a specific production strain from an MB Pharma collection and suitable culturing conditions, sufficient production of the required enzymes occurs. A combination of collagenase produced by the specific strain of *Clostridium histolyticum* and the implementation of optimum conditions of collagenase purification is unique. At first, we stabilize the enzyme through dialysis to a buffer of a higher pH (8), which is more natural for *Clostridium histolyticum* collagenase than physiological pH in the above-mentioned one. Only through gradual dialysis to buffers of a lower pH, fluent transition to physiological conditions more appropriate for clinical practice, is ensured. Crude collagenase enzymes produced up to now lack sufficient efficacy for Langerhans islets (LI) isolation. This can be caused by poor production of individual proteins or incorrect preparation process. For high yield of LI, it is necessary to use highly efficient purified collagenase enzymes and mixtures of these enzymes. Combination of a new production strain CCM 8656 and circumscribed enzyme production procedures (see examples) enables the production of enzymatic mixture that is more efficient than the crude collagenases available and its efficacy is comparable to efficacy of purified collagenases mixture.

The objective of this invention is to provide a specific *Clostridium histolyticum* strain, the product of which, the collagenase enzyme, is obtained and in its final form can be used for cleavage of connective structures of the pancreas in order to receive vital Langerhans islets which can be used in a transplantation treatment of diabetes. Collagenase is a mixture of up to 12 proteolytic enzymes and other proteins received from a filtrate of *Clostridium histolyticum* cultures. Pancreas digestion is performed in an isolation chamber which was designed by Dr. Ricordi et al. and which is used in almost all isolation centres (Berková Z., Zacharovová K., Kříž J., Jirák D., Girman P., Dovolilová E., Koblas T., Hájek M., Saudek F.: The impact of islet labeling with superparamagnetic nanoparticles for magnetic resonance imaging on islet vitality; 10th world congress of IPITA, Geneva, Switzerland, 4.-7.5.2005). It is a closed system in which a collagenase solution circulates, and while it is slightly agitated, the cells release gradually.

SUMMARY OF THE INVENTION

The substance of the solution is bacterium *Clostridium histolyticum* CCM 8656 producing collagenase. Collagenase produced by the strain has the following characteristics: It is a mixture of two collagenases, col 1 and col 2, produced by the strain of bacterium *Clostridium histolyticum* (CCM 8656) with molecular weight of 116 kDa and 126 kDa. The protein mixture contains collagenase and its natural degraded parts, which represent most of the dry matter in the final product. On gel SDS PAGE, both stripes must be apparent, and there is a possibility of occurrence of lower molecular weight fragments which still poses catalytic activity. Both types of collagenase consist of two peptide domains which are able on their own to decompose collagen. The rest of the protein consists of a binding domain which binds the whole enzyme to the substrate, and even though it increases its activity via bonding to collagen, it is not necessary for the activity. Smaller molecules of the catalytic domains thus complement the activity of relatively large molecule of the complete enzymes due to better diffusion. Collagenase must have specific activity higher than 700 PZS/g. This unit (PZS/g) is defined as a number of micromols of substrate degraded by one gram of enzyme within one minute at a temperature of 25° C. Clostripain activity may be also desirable; however, it is not a must. Clostripain may be the required admixture to the resulting collagenase mixture. Unit U/mg is such enzyme activity of clostripain which catalyses hydrolysis of 1 μmol of substrate (BAEE) in 1 minute at a temperature of 25° C., pH 7.6 and presence of 2.5 mmol/l DTT. The optimum value of activity should range within 1.2-1.45 U/mg. It is therefore a naturally produced mixture of collagenolytic enzymes prepared by partial purification (see examples) and this mixture is suitable for isolation of LI.

Another subject of the invention is the use of "crude collagenase" in the isolation of Langerhans islets.

EXAMPLES

The strain of bacterium *Clostridium histolyticum* with working identification MB 204 was deposited in the CCM Czech Collection of Microorganisms, Masaryk University, Faculty of Science, Kamenice 5, 625 00 Brno, Czech Republic on Dec. 4, 2015 under the conditions of the Budapest Treaty and was assigned accession number CCM 8656. The strain *Clostridium histolyticum* CCM 8656 which we have cultivated (via selection by long-term passaging) was obtained from a mixture of three strains that were obtained from a German collection of strains as strains DSM 627, 1126 and 2158.

Culturing is generally performed in a tryptone medium, suitable for sufficient production of collagenase: (Tryptone 60 g/l, peptone 1.5 g/l, NaCl 2.5 g/l, glucose 1.25 g/l, $Na_2HPO_4$ 3.4 g/l) pH 8.4, before inoculation, 100 μl of vitamin K of storage concentration 1% and 100 μl of L-cysteine of storage concentration 0.5 g/ml are added to the culturing medium. The culture is cultivated 24 hours at 37° C.±1° C. without agitation. In the strain, using controlled evolution and long-term passaging (adaptive laboratory evolution) (Dragosits M, Mattanovich D. Adaptive laboratory evolution—principles and applications for biotechnology. Microb Cell Factories. 2013; 12:64. doi:10.1186/1475-2859-12-64), one copy of the gene for collagenase was deleted. This selectively appropriate deletion was achieved using selective pressure and long-term culturing in a laboratory. Even despite this deletion, the strain is able to produce a large amount of both types of collagenases. It may be caused by a strong promotor which supplies production of genes from two points in the genome. Into the culturing medium collagen was added as a substrate, which supported selective production of the enzyme which should degrade it. Thus, natural selection of the strain which is used for production of bacterial collagenase was achieved. The composition of the tryptone medium suitable for sufficient production of collagenase with collagen is: (Tryptone 60 g/l, peptone 1.5 g/l, NaCl 2.5 g/l, glucose 1.25 g/l, $Na_2HPO_4$ 3.4 g/l, collagen 50 g/l) pH 8.4, before inoculation, 100 μl of vitamin K of storage concentration 1% and 100 μl L- of cysteine of storage concentration 0.5 g/ml are added into the cultivation medium. The culture is cultivated 72 hours at 37° C.±1° C. without agitation, ideally in anaerobic conditions. Genes encoding collagenase ColG and ColH were identified previously in *C. histolyticum* type strain JCM1403 (ATCC19401, DSM 2158) (Matsushita O, Jung C-M, Katayama S, Minami J, Takahashi Y, Okabe A. Gene Duplication and Multiplicity of Collagenases in *Clostridium histolyticum*. J. Bacteriol. 1999; 181(3): 923-933; Yoshihara K, Matsushita O, Minami J, Okabe A. Cloning and nucleotide sequence analysis of the colH gene from *Clostridium histolyticum* encoding a collagenase and a gelatinase. J. Bacteriol. 1994; 176(21); 6489-6496). Production of 116 kDa collagenase and 98 kDa gelatinase was mentioned in Yoshirara et al. One of the collagenases produced by strain CCM 8656 differs in molecular weight (126 kDa) from the collagenase produced by the strain DSM 2158. Genes and their protein products are identical for the strains DSM 2158 and CCM 8656, but the comparison of crude collagenase production between these two strains (Table 1) shows higher efficacy of collagenase produced by CCM 8656. The whole genome sequence of DSM 2158 is not available and its comparison to the genome sequence of CCM 8656 is not possible. It is thus unclear what is the cause of the difference in collagenase efficacy. It is a markedly changed phenotypic manifestation though. In our experiments, the same procedure of collagenase production was used for both strains CCM 8656 and DSM 2158. The efficacy of collagenase produced by the strain DSM 2158 was always lower than 320 PZS/g and the yield of LI was poor (Table 1). The efficacy of collagenase produced by the strain CCM 8656 was always higher than 900 PZS/g and when this collagenase was used for LI isolation, the yield was higher than 1000 LI, the quality of LI was better and the time of isolation was shorter.

TABLE 1

Comparison of collagenases efficacy and their effect on LI isolation. CCM 8656, MB 201 and MB 202 are newly isolated strains and they are compared to collection strains and data from literature.

| Production Strain | Average Collagenase Efficacy PZS/g | Count of Isolated Langerhans islets (LI) | Note |
|---|---|---|---|
| MB 204 (CCM 8656) | >900 | >1000 | Newly isolated strain; our invention |
| MB 201 | <400 | <300 | Newly isolated strain |
| MB 202 | <400 | <400 | Newly isolated strain |
| DSM 1126 | <320 | <300 | Collection strain |
| DSM 2158 | <320 | <300 | Collection type strain with described collagenase genes |
| DSM 627 | <320 | <300 | Collection strain |
| VitaCyte | >1000 | >1000 | Control—highly efficient commercial purified collagenase |
| Sigma Aldrich | Different testing of efficacy | <300 | Data from literature**, crude collagenase |
| Dendo et al. | Different testing of efficacy | >1000 | Data from literature*, purified collagenase mixture |

*Dendo. M, Maeda H, Yamagata Y, Murayama K, Watanabe K, Imura T, Inagaki A, Igarashi Y, Katoh Y, Ebina M, Fujimori K, Igarashi K, Ohuchi N, Satomi S, Goto M., Synergistic Effect of Neutral Protease and Clostripain on Rat Pancreatic Islet Isolation. Transplantation. July 2015; 99(7):1349-55. doi: 10.1097/TP.0000000000000662.
**De Vos P, Smink A M, Paredes G, et al. Enzymes for Pancreatic Islet Isolation Impact Chemokine-Production and Polarization of Insulin-Producing β-Cells with Reduced Functional Survival of Immunoisolated Rat Islet-Allografts as a Consequence. Blondeau B, ed. PLoS ONE. 2016; 11(1):e0147992. doi: 10.1371/journal.pone.0147992.

Characteristics of strain *Clostridium histolyticum* CCM 8656 are: *Clostridium histolyticum* is an anaerobic gram-positive bacterium. Bacterial cells are mobile peritrichal straight rods with a size of 0.5-0.9×1.3-9.2 μm and they form in pairs or short chains. Cells are capable of sporulation; in anaerobic conditions their cell wall contains meso-DAP, glutamic acid and alanine. During cultivation on blood plates, colonies are large, reaching 0.5 to 2 mm in diameter, of circular to irregular shape, flat to slightly convex, of white-grey colour, glossy with granular surface mosaic. Similar colonies can be also cultivated in aerobic conditions, but considerably fewer colonies grow, which are much smaller. Therefore, cultivation is thus suitable mainly in anaerobic conditions, when a large amount of the required collagenase is produced. Bacteria are able to grow at temperatures from 25° C. to 45° C., but the optimum growth temperature is 37° C. The strain *Clostridium histolyticum* CCM 8656 is strongly proteolytic and produces considerable amounts of various proteolytic enzymes including collagenase, elastinase, neutral proteases and clostripain. The strains of this bacterium are sensitive to chloramphenicol, erythromycine and tetracycline. The strains are toxic, but in long cultivation, their precursor-proteases may degrade own toxins. Specific 16S RNA (GenBank accession number 16S rRNA of gene: M59094) shows that this strain is similar to the strains *Clostridium limosum* (97.2%) and *Clostridium proteolyticum* (96.1%).

Collagenase for isolation of Langerhans islets is received as a metabolite of the bacterium *Clostridium histolyticum*. This enzyme has a synergic effect in the process of degradation of collagen and other extracellular components. Collagenase for the isolation of Langerhans islets is generally appropriate for the isolation of cells from a number of animal tissues. The product is provided with basic information about enzymatic activity. The optimum concentration of enzyme and the specific conditions for using of degradation of various tissues has to be defined empirically. The enzyme is not of animal origin.

Collagenase for the isolation of Langerhans islets is suitable for cell separations of, e.g., tumour cells, separation of murine kidney cells, cells of lung tissue and various epithelial tissues. The enzyme also can be used for the isolation of hepatocytes. Considering the selective collagenolytic activity which primarily does not damage cell membranes, the enzyme can be used generally as a dispersing cell agent, also in the conditions of cell cultures. It is generally applicable that organs with a higher content of collagen can be incubated with collagenase for isolation of Langerhans islets for a longer time and at concentrations higher than when working with other proteolytic enzymes, without the cells losing their viability.

Alternative applications of collagenase according to the invention are in the preparation of various cell cultures, in the research of medicinal products based on enzymatic activity of collagenase and in the various transplantation programmes.

Example 1

Opening and Inoculating of a Cab

Bacterial culture *Clostridium histolyticum* strain No. CCM 8656 is stored in a freezing medium at −80° C. or in a form of lyophilizate in a glass vial at 4° C. 100 μl of de-frost culture is inoculated to 100 ml of a liquid medium which is sterilized immediately before inoculation and then temperature-adjusted to a temperature of 37° C. The culture medium, suitable for cultivation of anaerobic bacteria is thus deaerated. The composition of tryptone medium suitable for sufficient production of collagenase is: (Tryptone 60 g/l, peptone 1.5 g/l, NaCl 2.5 g/l, glucose 1.25 g/l, $Na_2HPO_4$ 3.4 g/l) pH 7.8, before inoculation, 100 μl of vitamin K of storage concentration 1% and 100 μl of L-cysteine of storage concentration 0.5 g/ml are added to the culturing medium. The culture is cultivated 24 hours at 37° C.±1° C. without agitation. After cultivation, purity of bacterial strains is verified through growth on solid media (anaerobic cultivation) and morphology of cells is assessed microscopically.

Preparation of Large-Scale Cultivation:

Bacterial culture *Clostridium histolyticum* strain No. 8656 cultivated in 100 ml of medium is collected from the bottom part of a bottle. 5 ml of culture is inoculated to 500 ml of a liquid medium which is sterilized immediately before inoculation and then temperature-adjusted to a temperature of 37° C. The culture medium, suitable for cultivation of anaerobic bacteria is thus deaerated. The composition of tryptone medium suitable for sufficient production of collagenase is: (Tryptone 60 g/l, peptone 1.5 g/l, NaCl 2.5 g/l, glucose 1.25 g/l, $Na_2HPO_4$ 3.4 g/l) pH 7.8, before inoculation, 100 μl of vitamin K of storage concentration 1% and 100 μl of L-cysteine of storage concentration 0.5 g/ml are added to the culturing medium. The culture is cultivated 24 hours at 37° C.±1° C. without agitation.

Cultivation in Fermentor:

19 litres of cultivation medium is prepared in a fermentor (Tryptone 60 g/l, peptone 1.5 g/l, NaCl 2.5 g/l, glucose 1.25 g/l, $Na_2HPO_4$ 3.4 g/l) pH 7.8, before inoculation, 20 ml of vitamin K of storage concentration 1% and 20 ml of L-cysteine of storage concentration 0.5 g/ml are added. Fermentor is inoculated with 500 ml of bacterial culture from the previous step of cultivation. Mixed inoculum is sucked aseptically to the prepared cultivation medium. After inoculation, sample 0 is taken. Culturing proceeds at +37° C.+1° C. Culturing conditions are adjusted depending on bacterial growth. Once cultivation starts, the pH is adjusted on a continuous basis with a 2M solution of NaOH to a value of 7.8±0.5. Culturing proceeds without stirring or aeration.

Cultivation is finished if two consecutive samplings do not show a significant increment and the pH does not change. If at least the pH changes, cultivation lasts for 40-48 hours.

Processing of Enzyme:

When culturing is completed, 20 litres of the culture medium containing both bacteria and raw collagenase is drained into an appropriate vessel with 9.46 kg ammonium sulphate. The whole mixture is stirred so that ammonium sulphate is dissolved; the pH is then adjusted to a value of 6.8-7.6. The mixture is left to sediment for 4-7 days at 4° C. After 4-7 days, supernatant is sucked off using a peristaltic pump while the maximum volume of sediment is preserved without stirring it. Sediment containing precipitated collagenase is transferred to dialysing hoses (approx. 0.3-1 litre of sediment). The dialysing hose is placed in 10 l of buffer Tris Cl (Tris 0.75 g/l, $CaCl_2$ 0.484 g/l, pH 10) and left to dialyse for 3 hours. Then the buffer is replaced with other 10 l of TRIS HCl for 24 hours. Then the buffer is replaced with 10 l of TRIS HCl of a different pH (Tris 0.36 g/l, $CaCl_2$ 0.242 g/l, pH 7.5-8.5) for 24 hours. Then it is again replaced with fresh Tris III. If dialysate appears to be too thick, replacement of the Tris buffer may be done two more times within a further 24 hours.

When dialysis is completed, the content of the dialysing hoses is poured out to cuvettes and centrifugated (3500×g) for 45 minutes. Supernatant is poured into a sterile vessel and filtered through a 0.45 μm filter. The ultrafiltration in cartridges Millipore 50 kDa follows. Using this method leads to concentrating and reducing of the lysate volume. When collagenase is concentrated to the volume of 120 ml, filtration through a 0.45 μm filter is performed. Then filling in vials and lyophilisation of the product follows.

Example 2

Inoculation and culturing of bacterial strain *Clostridium histolyticum* CCM 8656 is the same as in Example 1. When culturing in the fermentor is completed, bacteria *C. histolyticum* is removed by centrifugation (7000×g) and precipitation of collagenase with ammonium sulphate is performed only in supernatant. Precipitate containing sulphate with precipitated protein is left to sediment for 4-6 days at 4° C. After dialysis against buffering solutions, Tris HCl buffers (the same buffers as in Example 1), then ultrafiltration follows again in cartridges millipore with "cut off" 50 kDa. When the protein is thickened, the sample is filled by 10 ml in vials and lyophilised.

Example 3

Inoculation and culturing of bacterial strain *Clostridium histolyticum* CCM 8656 is the same as in Example 1. However, dialysis is followed by ultrafiltration through ultrafiltration cartridges, at first with "cut-off" 300 kDa for removal of ballast proteins of a large molecular weight. Thus, volume is increased because flow-through is maintained and then the solution is ultrafiltrated in a cartridge "cut off" 50 kDa for removal of smaller proteins and degraded parts. In the course of concentrating, Tris-HCl buffer (Tris 0.36 g/l, $CaCl_2$ 0.242 g/l, pH 7.5-8.5) is continuously added. When the protein is thickened, the sample is filled by 10 ml in vials and lyophilised.

Example 4

Inoculation and culturing of bacterial strain *Clostridium histolyticum* CCM 8656 is the same as in Example 1. When culturing in the fermentor is completed, bacteria *Clostridium histolyticum* are removed by centrifugation (7000×g). However, in this case, precipitation with ammonium sulphate is not used; protein is directly thickened. Through ultrafiltration cartridges at first with "cut off" 300 kDa ballast proteins of a large molecular weight are removed. Thus, volume is increased because flow-through is maintained and then the solution is ultrafiltered in a cartridge with "cut off" 50 kDa for the removal of smaller proteins and degraded parts, and the volume is reduced. When the protein is thickened, the sample is filled by 10 ml in vials and lyophilised.

Method:

Individual preparation methods for optimal production and purification of desired enzymes from the strain CCM 8656 are described in individual examples in this document. The mixture of enzymes, produced directly from bacterial culture, that leads to efficient LI isolation is also mentioned. A few methods of collagenase purification using precipitation with ammonium sulphate have been described. However, we use different concentrations for optimal removal of undesired ballast proteins and preserving of enzymatically active proteins (clostripain and neutral protease) to support characteristics of the final collagenase, for its use in the isolation of Langerhans islets. The method uses only precipitation with ammonium sulphate, dialysis and an ultrafiltration system, which is a simple, easy-to-do method, compared to the costly and demanding purification method using chromatography. Moreover, large collagenase volumes can be processed using this method, compared to chromatographic methods. This method preserves other proteins which, in a proper ratio, support collagenase activity. Since the bacterial culture is processed in the production, the intracellular proteins get to the final product. In other cases, only the supernatant after culturing is processed, and here the supporting enzymes are lost. The method is also innovative in using two pH values, at first precipitate is dialysed against a buffer of a high pH. This process has been implemented in order to increase protein stability and achieve a higher yield. Dendo et al. (2015) demonstrates that the synergy of collagenase and clostripain positively affects the amount of LI obtained from the pancreases of experimental animals. The combination of enzymes causes high yield>1000 LI, similarly as in the case of our crude collagenase (Table 1). But the publication deals with highly purified recombinant proteins. The collagenase mentioned in the publication is not produced directly from *C. histolyticum*, it is a GMO product—a recombinant protein produced in *E. coli*. Adjusting to the desired concentration is performed separately for each enzyme. In our case, the mixture of enzymes comes directly from the specific strain *C. histolyticum* CCM 8656 and the quality of the mixture, shown by the amount of isolated LI, is comparable to recombinant collagenase. The advantage of natural collagenase production is the possibility of (legislatively) easier process of production and application in clinical and laboratory practice than in the case of GMO products, recombinant proteins. More studies focus on the appropriate ratio of collagenases and other enzymes used for LI isolation. All of them agree on achieving the highest efficacy by mixing purified collagenases, neutral proteases, clostripain, etc. In our case, the mixture of crude collagenase is similarly effective for LI isolation as the mixture of individually purified enzymes.

Using crude collagenases always leads to lower yields of LI, as illustrated by Vos et al., 2016 (Table 1). At the beginning of discussion of this publication, different contradictory studies discussing the role of neutral proteases are mentioned. The authors suggest that mixture of enzymes could be contaminated by undesirable enzymes. In our case, the resulting product is an enzymatic mixture with parameters comparable to a mixture of purified collagenases and other proteases.

Sequencing and PCR of the Gene for Collagenase:

Before preparing the DNA for sequencing, it was necessary to verify which of the possible types of collagenase is produced by the strain used for production. Based on the similarity and the origin of the strains, a gene for collagenase with the size of 3967 bp was selected. For the selected sequence a pair of primers for PCR (polymerase chain reaction) was suggested (KG Up: GGGATTATCTAT-GAAAAAAAA, KG Low: AATTATTTATTTACCCT-TAACTCA) and PCR for confirmation of the gene in the bacterium genome was performed. The reaction confirmed the presence of the just selected gene which enabled us to identify the protein product of the gene for other analyses of protein. Mainly the sequence of the amino acids and the size of protein (126 kDa) were important.

The collection of applicant MB PHARMA s.r.o. currently disposes of three strains of bacterium *Clostridium histolyticum*, which produce not only bacterial collagenase but also a significant amount of clostripain and neutral proteases. These enzymes may, but may not be, required for the production of the final product. In the case that they are absent, they must be then added separately in order to isolate the Langerhans islets. Clostripain and neutral proteases are present in the mixture of proteins produced by *C. histolyticum* CCM 8656 using the methods mentioned above.

Working identification numbers of the three strains are: MB 201, MB 202 and MB 204 (CCM 8656), and for the purpose of the mass production the strain *Clostridium histolyticum*, MB 204 (CCM 8656) was selected. Although the gene for collagenase in this production strain was confirmed using PCR, for better characterization it is better to determine the whole sequence of genome DNA. Thus, the genes for clostripain and potential neutral proteases can be found. Therefore, to ensure successful sequencing, DNA of very good quality and concentration must be prepared. A large volume of data must be processed for sequencing, and finished sequences of contigs must be then annotated. All three strains of *C. histolyticum* were sequenced, and annotating of their genomes showed that they code genes of two types of collagenase—collagenase proved using PCR (col 2) and the second type of collagenase of molecular weight 116 kDa (col 1). Strain M 201 contained a gene for col 1 in two copies and a gene for col 2 in one copy only; on the contrary, strain MB 202 has a gene for col 1 in one copy and a gene for col 2 in two copies. The production strain MB 204 had both genes for col 1 and col 2 in one copy only.

Genomes of all strains include a gene for clostripain. This enzyme can help collagenase to better disintegrate tissues during isolation of Langerhans islets. The main component of the collagenase final mixture should be collagenase, while clostripain should be a minor component. This was demonstrated.

All strains of *Clostridium histolyticum* dispose of a gene for the production of clostripain, but alternatively, it would be more appropriate for the proper ratio of collagenase and clostripain to produce both enzymes separately and produce a mixture of the proper ratio just before the application. Clostripain has a molecular weight of 43.4 kDa, so it would be possible to produce it relatively easily also as a recombinant protein, e.g., in *E. coli*. Our strain *Clostridium histolyticum* CCM 8656 produces clostripain in an optimal amount to support the efficacy of collagenase in LI isolation.

It is a mixture of two collagenases, col 1 and col 2, produced by the bacterium *Clostridium histolyticum* CCM 8656 with a molecular weight of 116 kDa and 126 kDa.

Col 1, Mw: 116.3 kDa, pI: 5.82

SEQ ID NO: 1

MKRKCLSKRLMLAITMATIFTVNSTLPIYAAVDKNNATAAVQNESKRYTV

SYLKTLNYYDLVDLLVKTEIENLPDLFQYSSDAKEFYGNKTRMSFIMDEI

GRRAPQYTEIDHKGIPTLVEVVRAGFYLGFHNKELNEINKRSFKERVIPS

ILAIQKNPNFKLGTEVQDKIVSATGLLAGNETAPPEVVNNFTPILQDCIK

NIDRYALDDLKSKALFNVLAAPTYDITEYLRATKEKPENTPWYGKIDGFI

NELKKLALYGKINDNNSWIIDNGIYHIAPLGKLHSNNKIGIETLTEVMKV

YPYLSMQHLQSADQIKRHYDSKDAEGNKIPLDKFKKEGKEKYCPKTYTFD

DGKVIIKAGARVEEEKVKRLYWASKEVNSQFFRVYGIDKPLEEGNPDDIL

TMVIYNSPEEYKLNSVLYGYDTNNGGMYIEPEGTFFTYEREAQESTYTLE

ELFRHEYTHYLQGRYAVPGQWGRTKLYDNDRLTWYEEGGAELFAGSTRTS

GILPRKSIVSNIHNTTRNNRYKLSDTVHSKYGASFEFYNYACMFMDYMYN

KDMGILNKLNDLAKNNDVDGYDNYIRDLSSNYALNDKYQDHMQERIDNYE

NLTVPFVADDYLVRHAYKNPNEIYSEISEVAKLKDAKSEVKKSQYFSTFT

LRGSYTGGASKGKLEDQKAMNKFIDDSLKKLDTYSWSGYKTLTAYFTNYK

VDSSNRVTYDVVFHGYLPNEGDSKNSLPYGKINGTYKGTEKEKIKFSSEG

SFDPDGKIVSYEWDFGDGNKSNEENPEHSYDKVGTYTVKLKVTDDKGESS

VSTTTAEIKDLSENKLPVIYMHVPKSGALNQKVVFYGKGTYDPDGSIAGY

QWDFGDGSDFSSEQNPSHVYTKKGEYTVTLRVMDSSGQMSEKTMKIKITD

-continued

PVYPIGTEKEPNNSKETASGPIVPGIPVSGTIENTSDQDYFYFDVITPGE

VKIDINKLGYGGATWVVYDENNNAVSYATDDGQNLSGKFKADKPGRYYIH

LYMFNGSYMPYRINIEGSVGR

Col 2, Mw: 126.2, pI: 5.62

SEQ ID NO: 2
MKKNILKILMDSYSKESKIQTVRRVTSVSLLAVYLTMNTSSLVLAKPIEN

TNDTSIKNVEKLRNAPNEENSKKVEDSKNDKVEHVKNIEEAKVEQVAPEV

KSKSTLRSASIANTNSEKYDFEYLNGLSYTELTNLIKNIKWNQINGLFNY

STGSQKFFGDKNRVQAIINALQESGRTYTANDMKGIETFTEVLRAGFYLG

YYNDGLSYLNDRNFQDKCIPAMIAIQKNPNFKLGTAVQDEVITSLGKLIG

NASANAEVVNNCVPVLKQFRENLNQYAPDYVKGTAVNELIKGIEFDFSGA

AYEKDVKTMPWYGKIDPFINELKALGLYGNITSATEWASDVGIYYLSKFG

LYSTNRNDIVQSLEKAVDMYKYGKIAFVAMERITWDYDGIGSNGKKVDHD

KFLDDAEKHYLPKTYTFDNGTFIIRAGDKVSEEKIKRLYWASREVKSQFH

RVVGNDKALEVGNADDVLTMKIFNSPEEYKFNTNINGVSTDNGGLYIEPR

GTFYTYERTPQQSIFSLEELFRHEYTHYLQARYLVDGLWGQGPFYEKNRL

TWFDEGTAEFFAGSTRTSGVLPRKSILGYLAKDKVDHRYSLKKTLNSGYD

DSDWMFYNYGFAVAHYLYEKDMPTFIKMNKAILNTDVKSYDEIIKKLSDD

ANKNTEYQNHIQELADKYQGAGIPLVSDDYLKDHGYKKASEVYSEISKAA

SLTNTSVTAEKSQYFNTFTLRGTYTGETSKGEFKDWDEMSKKLDGTLESL

AKNSWSGYKTLTAYFTNYRVTSDNKVQYDVVFHGVLTDNADISNNKAPIA

KVTGPSTGAVGRNIEFSGKDSKDEDGKIVSYDWDFGDGATSRGKNSVHAY

KKAGTYNVTLKVTDDKGATATESFTIEIKNEDTTTPITKEMEPNDDIKEA

NGPIVEGVTVKGDLNGSDDADTFYFDVKEDGDVTIELPYSGSSNFTWLVY

KEGDDQNHIASGIDKNNSKVGTFKSTKGRHYVFIYKHDSASNISYSLNIK

GLGNEKLKEKENNDSSDKATVIPNFNTTMQGSLLGDDSRDYYSFEVKEEG

EVNIELDKKDEFGVTWTLHPESNINDRITYGQVDGNKVSNKVKLRPGKYY

LLVYKYSGSGNYELRVNK

In the protein mixture, collagenase and its natural degraded parts represent most of the dry matter in the final product. It may also contain clostripain or neutral proteases detectable using an appropriate method for measuring of activity of those admixtures. However, the presence of both non-degraded collagenases and possibly their parts is essential. There must be two stripes visible on gel 12% SDS-PAGE, corresponding to the size 116 kDa and 126 kDa, and there is also a possibility of occurrence of a stripe of lower molecular weight protein, which still has catalytic activity. If zymogram is used, lytic zones of proteins of lower molecular weight may be visible. Smaller molecules of the catalytic domains thus complement activity of relatively large molecules of the complete enzymes due to better diffusion. Collagenase must have specific activity higher than 700 PZS/g. This unit is defined as a number of micromols of substrate degraded by one gram of enzyme within one minute at a temperature of 25° C. Clostripain activity may be also desirable; however, it is not a must. Clostripain may be the required admixture to the resulting collagenase mixture. Unit U/mg is such enzyme activity of clostripain which catalyses hydrolysis of 1 μmol of substrate (BAEE) in 1 minute at a temperature of 25° C., pH 7.6 and presence of 2.5 mmol/l DTT. The optimum value of activity should range within 1.2-1.45 U/mg.

Figure 1:
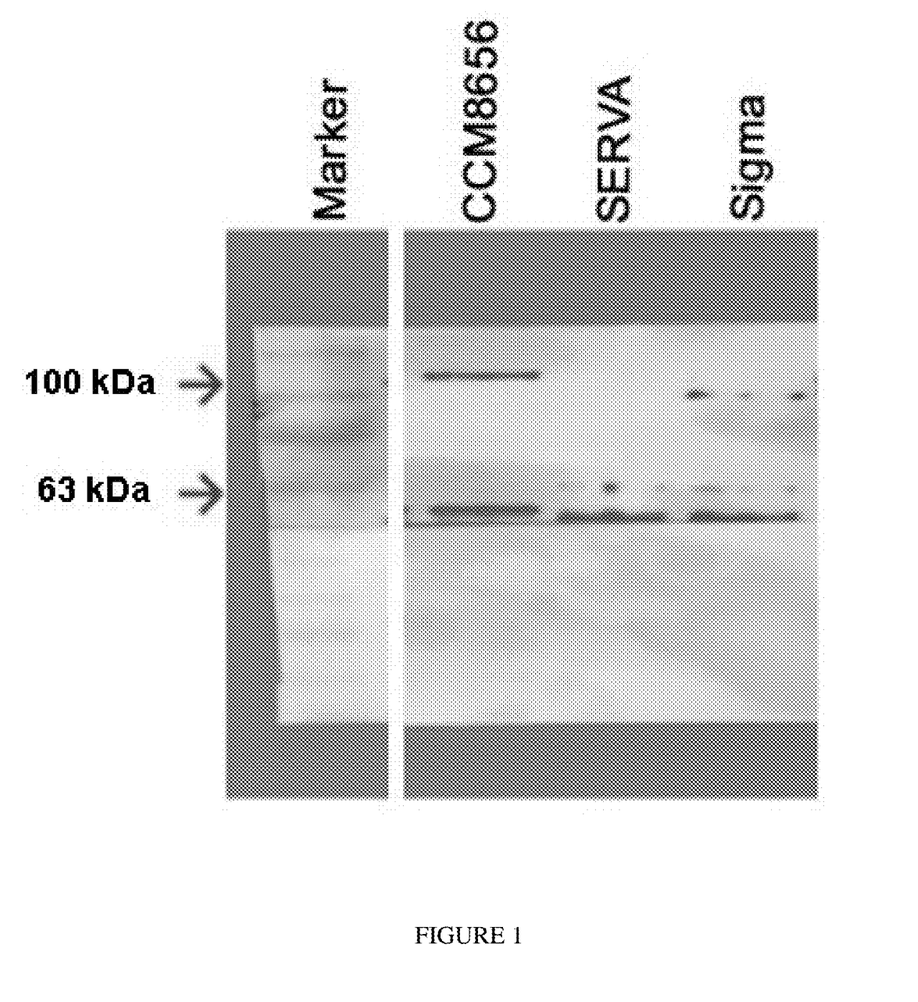
FIG. 1 is a Western blot of collagenase produced by the strain *Clostridium histolyticum* CCM 8656 and commercially-available collagenases.
Figure 2:
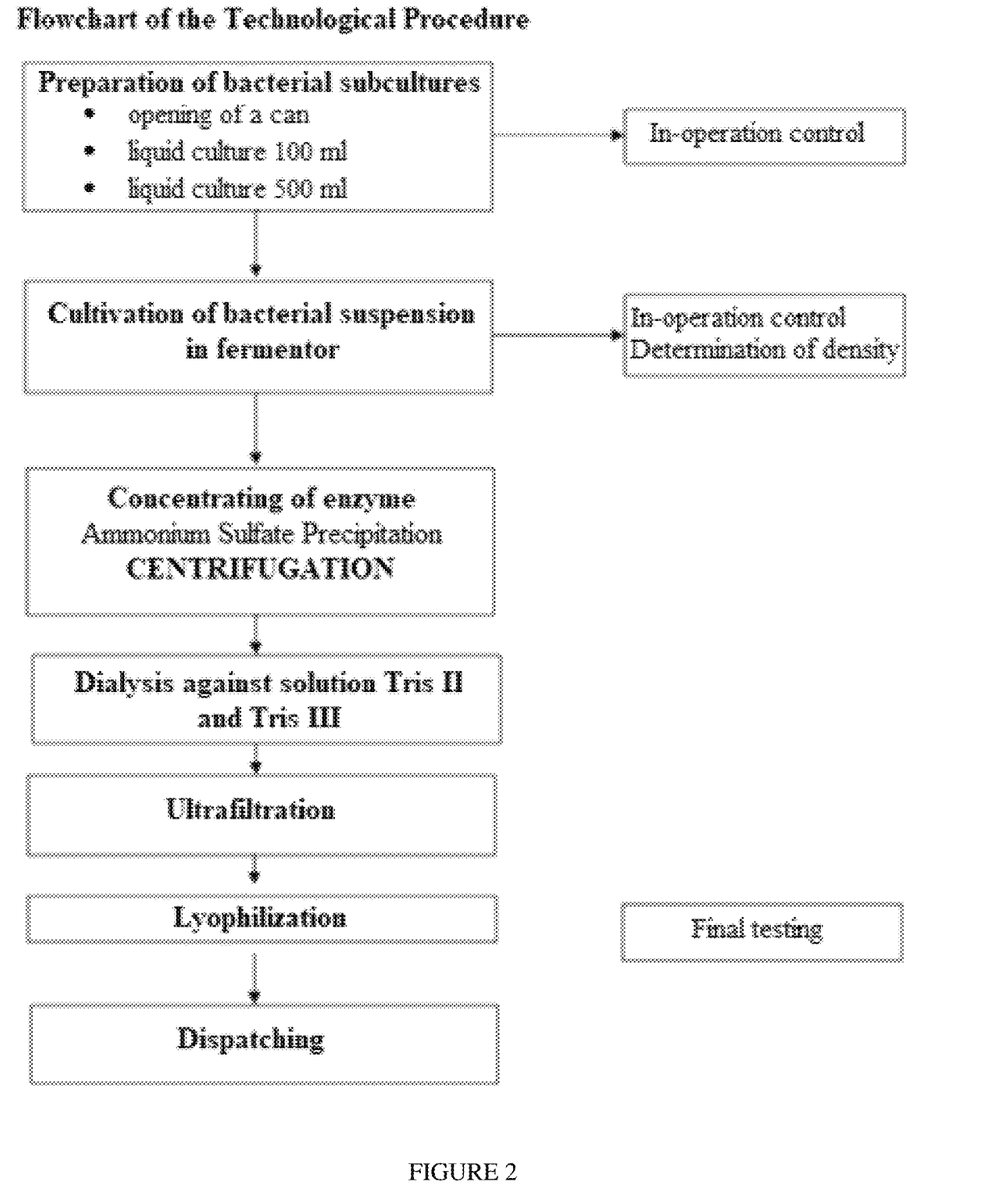
FIG. 2 is a flowchart of the technological procedure.

Strain *Clostridium histolyticum* MB 204 stored in the collection as CCM 8656 had a much higher yield of collagenase than other tested strains commonly used for the production of collagenase. For assessment of the optimal collagenase production procedure we compared the *C. histolyticum* strains DSM 627, 1126, 2158 and strains MB 201, MB 202 and MB 204. The mixture of enzymes produced from the strain MB 204 was significantly more efficient in LI isolation compared to the other tested strains. The gene encoding collagenase in MB 204 has the same nucleotide sequence as the analogous gene in the strain 2158, but the strain MB 204 produces a more efficient mixture of enzymes, thus a markedly different phenotypic manifestation is observed at equal cultivation conditions. Even though the genes encoding collagenase are identical in these two strains, the expression of the protein in the cell can be affected by various regulation mechanisms, in which the two strains differ. Although compared to commercially used bacteria this strain contains one copy of the gene for collagenase type I and one copy of the gene for collagenase type II; however, the yield of collagenase increased, most probably due to expression caused by a strong promotor. Moreover, the strain produces a minimal amount of toxic proteins, and during preparation, undesirable proteins are degraded, which is a big advantage for practical use in transplantation medicine.

The new method of production in combination with the new strain leads to the production of stable collagenase from *Clostridium histolyticum*. Cultivation of a relatively small volume gives sufficient yields of both types of collagenase in the final product. Although partial degradation occurs, it is more likely beneficial in combination with a sufficient amount of non-degraded part of the enzyme, as the degraded parts still retain their proteolytic activity.

Enzyme collagenase is used for the digestion of pancreatic tissue, during which Langerhans islets (LI) are released and can be used for the treatment of diabetes. Isolated LI using collagenase must meet strict criteria so that they can be transplanted to diabetic patients. The most important monitored parameters of isolation are as follows: duration of digestion, digestion quality, quality of separation of cells from exocrine tissue and quality of cells after isolation and culturing. Quality of cells is evaluated using dying of viable and dead cells, using glucose-stimulated secretion of insulin with beta cells of LI (expressed as stimulation index) and using measuring of oxygen consumption. Using collagenase according to the invention resulted in achieving the digestion time of 15 minutes and average yield of 1000 LI which retain sufficient vitality (more than 95%). This collagenase is thus suitable for isolation of LI for transplantation purposes.

In cases of collagenase production described in the literature (De Vos et al. 2016) the Sigma Aldrich crude collagenase from *C. histolyticum* was used, where the production process and *C. histolyticum* strain differs from ours. In the case of Sigma Aldrich collagenase, the enzymatic mixture containing collagenase, clostripain and neutral proteases is produced without producing individual components. However, the efficacy of the Sigma Aldrich collagenase is lower than the efficacy of our collagenase. The yield of LI 256 (±21) and 174 (±23) is lower than in the case of collagenase produced using our unique process and the strain CCM 8656 that allowed us to isolate 1147 (±231) LI. This result is similar to the result that was achieved using purified commercial collagenase (VitaCyte collagenase which does not contain clostripain and neutral proteases), when 905±257 LI were isolated. Table 1 likewise shows the great difference between Sigma Aldrich and VitaCyte collagenases. The efficacy of our collagenase is thus comparable rather to the efficacy of purified enzymes and the collagenase markedly differs from other crude enzymatic mixtures. This can be explained by using different production strain, different procedure and partial purification. Moreover, the authors of the publication say that individual batches of collagenase differ in efficacy. Due to our standardized procedure, we achieved similar efficacy among different batches. Western blot (FIG. 1) shows higher amount of nondegraded collagenase in our sample compared to the Sigma Aldrich collagenase. So far, yields of LI were poor when crude collagenase mixtures were used. For high yields of LI, using individually purified enzymes in mixtures was necessary, as described by Dendo et al. 2015. In our case, the highly efficient crude collagenase is produced using cultivation and partial purification from the unique *C. histolyticum* strain CCM 8656.

In the case of collagenase produced according to our invention (FIG. 1), it is clear that most of the enzyme is not degraded. The Western blot also shows that the SERVA collagenase is degraded and the Sigma Aldrich collagenase is partially degraded and the degradation is clearly higher than in the case of collagenase produced according to our invention.

The invention claimed is:

1. A bacterial strain *Clostridium histolyticum* deposited under deposit number CCM 8656, wherein said bacterial strain produces proteolytic enzymes comprising collagenase, elastinase, neutral proteases and clostripain under anaerobic conditions at a temperature from 25° C. to 45° C.

2. A method for producing a mixture of two collagenases, col 1 and col 2, with a respective molecular weight of 116 kDa and 126 kDa, the method comprising culturing the bacterial strain *Clostridium histolyticum* CCM 8656 of claim 1 under anaerobic conditions at a temperature from 25° C. to 45° C.

3. A method for producing a mixture of two collagenases, col 1 and col 2, with a respective molecular weight of 116 kDa and 126 kDa, and clostripain, the method comprising culturing the bacterial strain *Clostridium histolyticum* CCM 8656 of claim 1 under anaerobic conditions at a temperature from 25° C. to 45° C.

4. A method for isolating Langerhans islets, the method comprising:
   culturing the bacterial strain *Clostridium histolyticum* CCM 8656 of claim 1 under anaerobic conditions at a temperature from 25° C. to 45° C. to produce a mixture of two collagenases, col 1 and col 2, with a respective molecular weight of 116 kDa and 126 kDa,
   digesting pancreatic tissue with the mixture of the two collagenases to release the Langerhans islets from the pancreatic tissue, and
   isolating the released Langerhans islets.

5. A method for isolating Langerhans islets, the method comprising:
   culturing the bacterial strain *Clostridium histolyticum* CCM 8656 of claim 1 under anaerobic conditions at a temperature from 25° C. to 45° C. to produce a mixture of two collagenases, col 1 and col 2, with a respective molecular weight of 116 kDa and 126 kDa, and clostripain,
   digesting pancreatic tissue with the mixture of the two collagenases and clostripain to release the Langerhans islets from the pancreatic tissue, and
   isolating the released Langerhans islets.

* * * * *